(12) United States Patent
Egertsdotter et al.

(10) Patent No.: US 9,125,352 B2
(45) Date of Patent: Sep. 8, 2015

(54) METHOD FOR MATURING AND SYNCHRONIZING CONIFER SOMATIC EMBRYOS

(75) Inventors: Ulrika Egertsdotter, Marietta, GA (US); David Clapham, Uppsala (SE)

(73) Assignee: SweTree Technologies AB, Umeå (SE)

( * ) Notice: Subject to any disclaimer, the term of this patent is extended or adjusted under 35 U.S.C. 154(b) by 365 days.

(21) Appl. No.: 13/637,351

(22) PCT Filed: Mar. 29, 2011

(86) PCT No.: PCT/SE2011/050356
§ 371 (c)(1),
(2), (4) Date: Nov. 27, 2012

(87) PCT Pub. No.: WO2011/123038
PCT Pub. Date: Oct. 6, 2011

(65) Prior Publication Data
US 2013/0065306 A1    Mar. 14, 2013

Related U.S. Application Data

(60) Provisional application No. 61/318,801, filed on Mar. 30, 2010.

(30) Foreign Application Priority Data

Mar. 30, 2010    (SE) ...................................... 1050305

(51) Int. Cl.
*A01H 4/00* (2006.01)
*C12N 5/00* (2006.01)

(52) U.S. Cl.
CPC .............. *A01H 4/005* (2013.01); *C12N 5/0025* (2013.01)

(58) Field of Classification Search
CPC ....... A01H 4/005; A01H 4/008; C12N 5/0025
USPC ........................................................ 435/422
See application file for complete search history.

(56) References Cited

U.S. PATENT DOCUMENTS 4,957,866 A * 9/1990 Gupta et al. ................... 435/422

FOREIGN PATENT DOCUMENTS

EP    1491089 A1    12/2004
WO    96/37096 A1    11/1996

OTHER PUBLICATIONS

Pullman et al. Improving loblolly pine somatic embryo maturation: comparidon of somatic and zygotic embryo morphology, germination, and gene expression. Plant Cell Rep (2003) 21:747-758.*
Roberts. Abscisic acid and mannitol promote early development, maturation and storage protein accumination in somatic embryos of interior spruce. Physiologia Plantarum 83: 247-254, 1991.*
International Search Report and Written Opinion received for PCT Patent Application No. PCT/SE2011/050356, mailed on Aug. 17, 2011, 11 pages.
Belmonte et al., "Alterations of the Glutathione Redox State Improve Apical Meristem Structure and Somatic Embryo Quality in White Spruce (Picea Glauca)", Journal of Experimental Botany, vol. 56, No. 419, Sep. 2005, pp. 2355-2364.
Burg et al., "Developmental and Genetic Variation in Nuclear Microsatellite Stability during Somatic Embryogenesis in Pine", Journal of Experimental Botany, vol. 58, No. 3, 2007, pp. 687-698.
Clapham et al "Gene Transfer by Particle Bombardment to Embryonic Cultures of Picea Abies and the Production of Transgenic Platlets", Scand. J. For. Res., vol. 15, 2000, pp. 151-160.
Garin et al., "Effect of Sugars, Amino Acids, and Culture Technique on Maturation of Somatic Embryos of Pinus Strobus on Medium with two Gellan Gum Concentrations", Plant Cell. Tissue and Organ Culture, vol. 62, 2000, pp. 27-37.
Nadel et al., "Regulation of Somatic Embryogenesis in Celery Cell Suspensions", Plant Cell, Tissue and Organ Culture, vol. 18, 1989, pp. 181-189.
Pullman et al., "Conifer Embryogenic Tissue Initiation: Improvements by Supplementation of Medium with D-Xylose and D-Chiro-Inositol", Tree Physiology, vol. 29, Dec. 5, 2008, pp. 147-156.
Pullman et al., "Liquid Medium and Liquid Overlays Improve Embryogenic Tissue Initiation in Conifers", Plant Cell Rep., vol. 26, 2007, pp. 873-887.
Roberts, Dane R., "Abscisic Acid and Mannitol Promote Early Development, Maturation and Storage Protein Accumulation in Somatic Embryos of Interior Spruce", Physiologia Plantarum, vol. 83, 1991, pp. 247-254.
von Arnold et al., "Spruce Embryogenesis", Methods in Molecular Biology. vol. 427: Plant Embryogenesis, 2008, pp. 31-47.
Emons et al., "The Influence of Sucrose, Mannitol, L-Proline, Abscisic Acid and Gibberellic Acid on the Maturation of Somatic Embryons of *Zea mays* L. from Suspension Cultures", J. Plant Physiol., vol. 142, 1993, pp. 597-604.
Extended European Search Report and European Search Opinion received for European Patent Application No. 11763150.7, mailed on Aug. 21, 2013, 6 pages.
Belmonte et al., "The Effect of Osmoticum on Ascorbate and Glutathione Metabolism During White Spruce (*Picea glauca*) Somatic Embryo Development", Plant Physiology and Biochemistry, vol. 43, 2005, pp. 337-346.
Tremblay et al., "Maturation of Black Spruce Somatic Embryos: Sucrose Hydrolysis and Resulting Osmotic Pressure of the Medium", Plant Cell Tissue and Organ Culture, vol. 42, 1995, pp. 39-46.

* cited by examiner

*Primary Examiner* — June Hwu
(74) *Attorney, Agent, or Firm* — Morrison & Foerster LLP (57) ABSTRACT

A method for the culture of somatic plant embryos comprising contacting said embryos with a culture medium containing a plasmolytic or near plasmolytic concentration of a sugar alcohol or a combination of sugar alcohols; and culturing said embryos in said culture medium for a time period suitable for the desired level of maturation to be achieved. Inositol is a preferable sugar alcohol.

13 Claims, 9 Drawing Sheets

METHOD FOR MATURING AND SYNCHRONIZING CONIFER SOMATIC EMBRYOS

CROSS REFERENCE TO RELATED APPLICATIONS

This is a U.S. National Phase patent application of PCT/SE2011/050356, filed Mar. 29, 2011, which claims priority to the U.S. Provisional Patent Application No. 61/318,801, filed Mar. 30, 2010, and the Swedish Patent Application No. 1050305-0, filed Mar. 30, 2010, each of which is hereby incorporated by reference in the present disclosure in its entirety.

FIELD OF THE INVENTION

The invention relates to the field of somatic plant embryo production, particularly to a method and a medium for maturing and synchronizing conifer somatic embryos.

BACKGROUND TO THE INVENTION

Plant Somatic Embryogenesis

Somatic embryogenesis in plants is a process in which somatic embryos are formed from somatic cells of plant tissue, usually an explant in vitro. The somatic embryos formed are genetically identical copies of the plant providing the initial explant. The process of somatic embryogenesis thereby offers a tool to obtain large numbers of genotypically identical plants for multiplication of selected genotypes of commercial interest, for conservation of endangered species or for generating genetically uniform plant material for research purposes.

Somatic embryogenesis is of special interest with regard to coniferous trees. Conifers of economic importance have long generation times, so that breeding through crossing and selection proceeds very slowly. Conifers are wind-pollinated over long distances and are highly heterozygous, so that the offspring of selected individuals is highly variable. Self-pollination, leading to greater homozygosity and uniformity of the offspring, is possible in principle but undesirable in practice owing to pronounced inbreeding depression. Multiplication of selected or elite individuals by somatic embryogenesis offers an attractive solution to these problems. For some species, particularly spruces, the procedure works well on a laboratory scale, but at present sexual propagation via seeds is the only cost-effective method for propagation. This situation could in principle be changed by simplifying and automating the laboratory procedures but several major challenges remain.

Methods for Somatic Embryogenesis

Plant regeneration through somatic embryogenesis in e.g. conifers consists of a series of consecutive steps (see e.g. von Arnold S, Clapham D. Spruce embryogenesis. 2008. *Methods Mol Biol.* 2008; 427:31-47;, Belmonte M F, Donald G, Reid D M, Yeung E C and Stasolla C. 2005. Alterations of the glutathione redox state improve apical meristem structure and somatic embryo quality in white spruce (*Picea glauca*). *J Exp Bot,*, Vol. 56,, No. 419,, pp. 2355-2364).

Taking Norway spruce as an example, the step 1, is initiation of an embryogenic culture from an explant, usually a mature or immature embryo, though there are reports of successful initiation from buds from adult trees. This step is carried out on a plant culture medium containing plant growth regulators, usually an auxin and a cytokinin. For step 2, continued proliferation, the initiated cultures are usually subcultured on essentially the same medium as for initiation. At this stage, the proliferating cell masses consist of more or less well differentiated immature somatic embryos, which morphologically correspond to a stage found in the developing seed in the early phase of seed development. The somatic embryos do not undergo any further development during proliferation and mature embryos are not formed during this phase.

In order to obtain embryo maturation, embryogenic cultures are usually transferred to a culture medium where auxin and cytokinin are omitted for step 3, known as prematuration. After about three to seven days of prematuration, during which the influences of auxin and cytokinin are lost, the prematured cultures are transferred to a maturation medium containing abscisic acid (ABA) for step 4, maturation. One characteristic of prematuration stage embryos is that the somatic embryos at this stage lack root meristems.

Step 5 involves partial drying of the embryos under high humidity, which is thought to partly mimic the natural drying of zygotic embryos in the seed and to improve subsequent conversion to plantlets. On a laboratory scale the embryos are picked out by hand using forceps and transferred to a small sterile petri dish. This is then placed in a larger petri dish containing sterile water to raise the humidity. After this step, the embryos are germinated in culture medium and start growing roots. In the final step 6, the embryos are converted into plantlets, separately or in combination with transfer to non-sterile cultivation in pots or containers in a greenhouse.

These six steps are briefly summarized in Table 1, below.

| Step | | Growth media (important component/s) | Somatic embryo characteristics |
|---|---|---|---|
| 1 | Initiation | Plant growth regulators | Proembryonic masses develop from embryo explants |
| 2 | Proliferation | The same media as step 1 | Proembryonic masses proliferate as 'callus' |
| 3 | Prematuration (~1 week) | All plant growth regulators are removed. | Transition from proembryo to embryo; no organized shoot and root meristems |
| 4 | Early maturation (3-5 weeks) | Initiated with abscisic acid | Embryos enlarge; shoot and root meristems organize; cotyledons just visible in some embryos at end of step. |
| 5 | Late maturation | Continue with abscisic acid; suitable stage for enhanced sugar alcohol treatment according to the present invention. | Further embryo enlargement, and devlopment of meristems and vascular tissue; cotyledons expand and separate. |
| 6 | Germination to plantlets | Medium lacks growth regulators | Root growth, extension of hypocotyl and cotyledons, greening. |

With regard to the above discussion of prior art, the invention addresses in particular the following issues with present somatic embryo maturation methods:

(1) The variable quality of the mature somatic embryos. A considerable fraction, perhaps 50%, of the embryos exposed to maturation medium, is incapable of conversion to rooted plantlets. The most promising embryos can be selected visually, so that around 90% of the selected embryos can be converted to rooted plantlets growing on sterile medium in petri dishes. Of these, some grow slowly so that at planting-out time, only about 75% of the selected embryos are suitable for transfer to greenhouse conditions. Thus there is a need for methods providing improved quality of somatic embryos, in particular in terms of uniformity of the quality.

(2) The unsynchronized development of the embryos exposed to maturation medium. The fraction of embryos that are suitable for conversion do not normally develop synchronously. Furthermore, by the time the slowly developing embryos have reached maturity, most of the fast developers have proceeded to premature germination, which impairs the quality of subsequent conversion to plantlets. It is necessary either to sacrifice the late developers, or harvest the embryos on two or more separate occasions. Thus there is a need for methods achieving synchronized maturation of somatic embryos and need for methods that prevent premature germination.

(3) Partial drying of the mature somatic embryos under high humidity. This step may be problematic, it adds to the labor involved and it would be advantageous if it could be omitted. Thus, there is need for streamlined methods that can dispense with the partial drying step.

It is therefore an object of the invention to provide methods to address the above-identified issues.

It is important to keep in mind that if industrial-scale production of conifers via somatic embryogenesis was used to produce a major fraction of the conifers planted yearly, the production scale would be in the hundreds of millions of plantlets annually. Thus, even relatively small improvements to the process may have significant economic impact.

Definitions

The terms somatic embryo and somatic plant embryo are used interchangeably. The terms refer to plant embryos derived from somatic tissue of a plant.

Norway spruce is a spruce species with the Latin name *Picea abies*, native to Europe.

The term sugar alcohol refers to a hydrogenated form of a sugar carbohydrate, whose carbonyl group (aldehyde or ketone of a reducing sugar) has been reduced to a primary or secondary hydroxyl group. Examples of sugar alcohols include: Glycol, Glycerol, Erythritol, Threitol. Arabitol, Xylitol, Ribitol, Mannitol, Sorbitol, Dulcitol, Iditol, inositol, Isomalt, Maltitol, Lactitol, Polyglycitol.

Inositol or cyclohexane-1,2,3,4,5,6-hexol is a sugar alcohol having the formula $C_6H_{12}O_6$, or $(-CHOH-)_6$. It has nine possible stereoisomers including cis-1,2,3,5-trans-4,6-cyclohexanehexol, or myo-inositol.

Myo-inositol

Plasmolysis is the process in plant cells where the plasma membrane pulls away from the cell wall due to the loss of water through osmosis, when the cell is exposed to hypertonic medium.

Plasmolytic concentration of a compound is the smallest concentration of said compound in a culture media that is sufficient to induce plasmolysis in plant cells cultured in said culture media.

The related term "near plasmolytic concentration" relates to a concentration that is somewhat below or above the plasmolytic concentration. Preferably, the near plasmolytic concentration is 50-150% of the plasmolytic concentration. More preferably the near plasmolytic concentration is 80-120% of the plasmolytic concentration, even more preferably 90-110% or higher, most preferably at 95-105%.

BRIEF DESCRIPTION OF THE DRAWINGS

In all figures the X-axis represent the different molarity of the sugar alcohol used.

SUMMARY OF THE INVENTION

In a first aspect, the present invention discloses a method for maturing somatic plant embryos in culture comprising the steps of:
a) Contacting said embryos with a culture medium containing a plasmolytic or near plasmolytic concentration of a sugar alcohol or a combination of sugar alcohols; and
b) Culturing said embryos in said culture medium for a time period such that the desired level of maturation is achieved.

Preferably, the concentration of the sugar alcohol or the combination of sugar alcohols in the culture medium is in the range of 0.1-0.5, M, preferably 0.2-0.3 M, most preferably 0.225-0.275, M.

Preferably, the sugar alcohol or the combination of sugar alcohols comprises one or more sugar alcohols selected from the group consisting of inositol (most preferably myo-inositol), glycerol, arabitol, xylitol, mannitol and sorbitol.

Preferably, at least 30, mol %, preferably at least 50, mol %, more preferably at least 80, mol %, most preferably at least 90, mol % of the sugar alcohol in the culture medium is comprised of inositol, most preferably myo-inositol.

Most preferably, the culture medium of the first aspect contains 0.2-0.3, M of myo-inositol.

Preferably, the somatic plant embryos at the time of contacting with the culture medium (step (a) of the method of the first aspect) are embryos having undergone a prematuration stage. A prematuration stage may comprise culture in a culture medium without auxin and cytokinin. A somatic embryo having undergone a prematuration stage may be characterized in that the embryo still lacks root meristems.

Also preferably, the somatic plant embryos at the time of contacting with the culture medium (step (a) of the method of the first aspect) are embryos not yet having fully undergone a germination stage. A somatic embryo not yet having undergone a germination stage may be characterized in that the embryo still lacks roots.

The somatic plant embryos in the method are preferably of a conifer species, preferably Norway spruce or pine, in particular loblolly pine.

The above method is preferably used for inhibiting premature germination of the somatic plant embryos.

The above method is also preferably used for synchronizing the maturation of the individual somatic plant embryos.

The above method is further preferably used for achieving uniform quality of the somatic plant embryos.

The above method is additionally preferably used for achieving uniform quality and synchronized development of somatic embryos-derived plantlets, preferably plantlets planted in a substrate. The substrate preferably comprises mineral wool.

In a second aspect, the invention discloses a method for producing plantlets from embryogenic mass, comprising the steps of:
 a) producing prematurated somatic embryos from embryogenic mass;
 b) maturating the prematurated somatic embryos using a method of the first aspect; and
 c) germinating the maturated embryos and converting the germinated embryos to platelets,
 wherein no partial drying of the maturated embryos takes place between the maturating and germination.

Preferably, the partial drying step that is omitted is a partial drying step under high humidity.

The said method of the first aspect may be one of the preferred variants of the method of the first aspect.

In a third aspect the invention also relates to use of a culture medium containing a plasmolytic or near plasmolytic concentration of a sugar alcohol or a combination of sugar alcohols for maturing somatic plant embryos in culture.

Preferably, the concentration of the sugar alcohol or the combination of sugar alcohols used is in the range of 0.1-0.5, M, preferably 0.2-0.3, M, most preferably 0.225-0.275, M.

Preferably, the sugar alcohol or the combination of sugar alcohols in the use comprises one or more sugar alcohols selected from the group consisting of inositol (preferably myo-inositol), glycerol, arabitol, xylitol, mannitol and sorbitol.

Preferably, at least 30, mol %, preferably at least 50, mol %, more preferably at least 80, mol %, most preferably at least 90, mol % of the sugar alcohols in the culture medium in the use is comprised of inositol, preferably myo-inositol.

Most preferably, the culture medium of the second aspect contains 0.2-0.3, M of myo-inositol.

Preferably, the somatic plant embryos at the time of initiation of the use are embryos having undergone a prematuration stage. A prematuration stage may comprise culture in a culture medium without auxin and cytokinin. A somatic embryo having undergone a prematuration stage may be characterized in that the embryo still lacks root meristems.

Also preferably, the somatic plant embryos at the time of initiation of the use are embryos not yet having fully undergone a germination stage. A somatic embryo not yet having undergone a germination stage may be characterized in that the embryo still lacks roots.

Preferably, the somatic plant embryos in the use are of a conifer species, preferably Norway spruce or pine, in particular loblolly pine.

Preferably, said culture medium is used for inhibiting premature germination of the somatic plant embryos.

Also preferably, said culture medium is used synchronizing maturation of the individual somatic plant embryos.

Further preferably, said culture medium is used achieving uniform quality of the somatic plant embryos.

The above use is preferably for achieving uniform quality and synchronized development of somatic embryos-derived plantlets, preferably plantlets planted in a substrate. The substrate preferably comprises mineral wool.

Detailed Description of the Invention

The invention is based on a serendipitous discovery. Gene transfer to spruce somatic embryos using a particle gun was experimented with, using a special medium originally designed for use with gene transfer for embryogenic cultures, containing 0.25, M myo-inositol. The resulting plasmolysis reduces damage during penetration by the gold particles, since it relaxes the tension in the cell membranes and minimizes tearing. By mistake, the somatic embryos were left in this medium for 12, days instead of returning them to the normal proliferation medium as intended. Surprisingly, the outcome from this culture was found to be superior to that usually obtained with the standard protocol, prompting further investigations.

Plasmolytic or near plasmolytic concentration of several sugar alcohols (inositol, mannitol, sorbitol) was found to induce synchronous maturation in the embryo cultures.

The synchronous maturation-effect was found to be related to the presence of a plasmolytic or near plasmolytic concentration of a sugar alcohol or a combination thereof in the culture medium. Without being bound by theory, it is conceivable that the high concentration of sugar alcohol(s) induces effect similar to partial drying by osmotically reducing the amount of water in the cytoplasm.

The use of high concentrations of inositol (specifically myo-inositol) in the culture media resulted in additional effects not seen with the other sugar alcohols tested. In addition to promoting uniform maturation, partly by inhibiting premature germination, inositol leads to the formation of more robust mature embryos with improved rooting capabilities. Furthermore, the inositol-treated embryos require no further partial drying before germination. Again, without being bound by theory, it is possible that the advantage that inositol possesses compared to other sugar alcohols is that it is taken up by the cells over a period of days. Consequently, the cells are first plasmolyzed and then gradually deplasmolyzed.

Inositol is also important in several aspects of cellular metabolism. Phytin, a constituent of protein bodies in cereal endosperm and in the extracellular supporting material of higher plant tissues, is the calcium/magnesium salt of phytic acid, a hexaphosphoric ester of inositol. Inositol is a constituent of lipids and of signaling molecules concerned with transport of molecules through membranes.

Thus, it is preferred that the sugar alcohols used in the invention are metabolically important by themselves (such as inositol or glycerol) or derivates of metabolically important sugars, such as xylose and arabinose, or both.

Therefore, it is preferable that at least a substantial fraction of the total sugar alcohol concentration is comprised of inositol, glycerol, arabinol, or xylitol, most preferably myo-inositol.

Desirable Quality Criteria for Matured Somatic Embryos

With help from guidance below, the skilled person will be able to distinguish somatic embryos having good quality from those of lesser quality.

The sides of the hypocotyls should be smooth and no swelling should be seen in the lower part of the hypocotyl of a good somatic embryo, a poor has a rough surface and is often swollen at the lower end. A good somatic embryo has moderately developed cotyledons with little greenish tone, and no root should be seen.

Figure 1A:
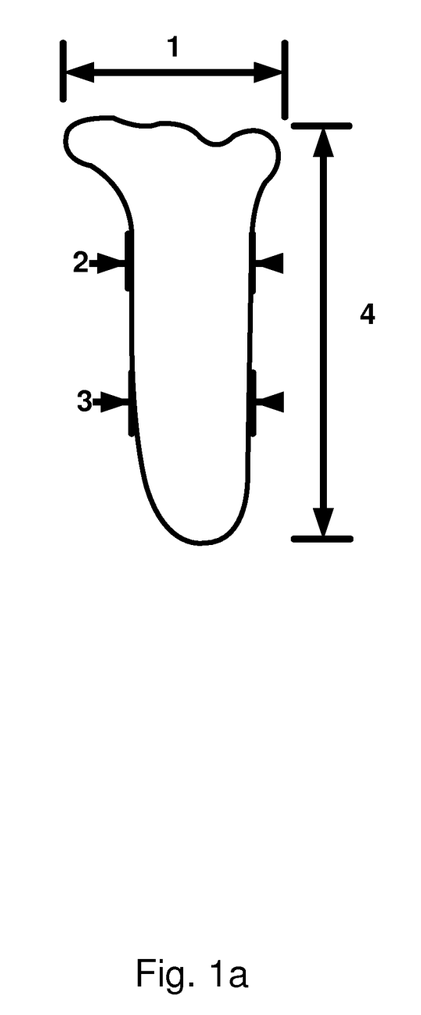
FIGS. 1a, and 1b, depict a number of relevant measures for assessing the quality of somatic embryos. See section titled "Desirable quality criteria for matured somatic embryos" for details.

In order to measure the quality of the somatic embryos, different measurements can be taken, see FIG. 1a, and table 2.

In poorly developed embryos, there is a tendency to constriction in the hypocotyl near the cotyledons and/or a swelling at the base of the hypocotyl, so that the ratio of widths one third down of the hypocotyl (2) to the width across the hypocotyl two thirds down the hypocotyl (3) is below unity, i.e. $(2)/(3) \geq 1$. In well developed embryos the ratio is just above unity.

TABLE 2

Figure 1B:
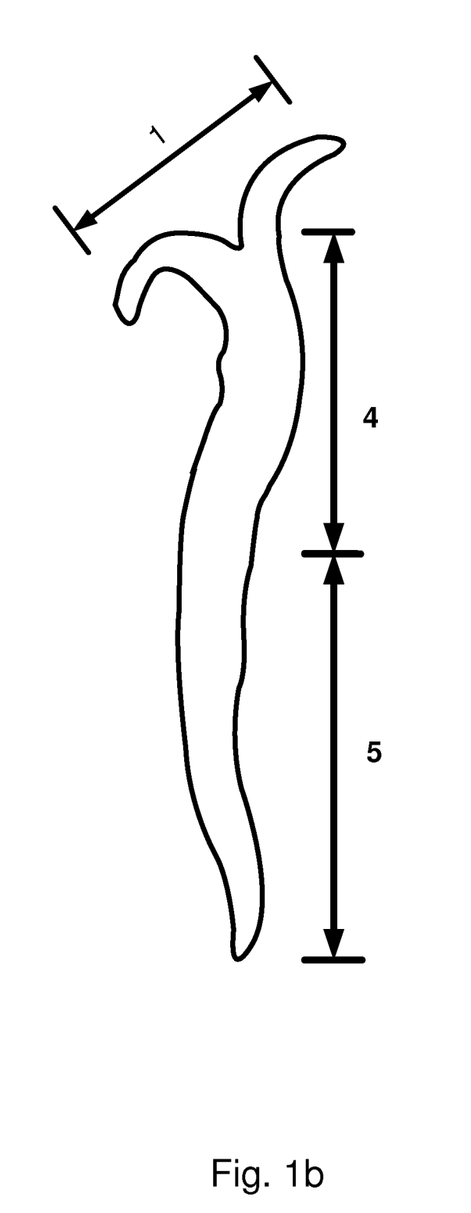
Figure 1C:
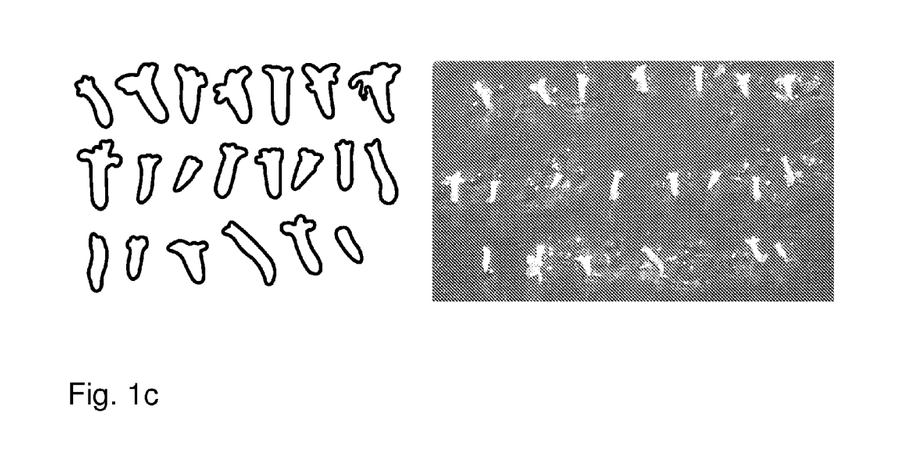
FIG. 1c, depict examples of high quality somatic embryos and FIG. 1d examples of bad quality somatic embryos.
Figure 1D:
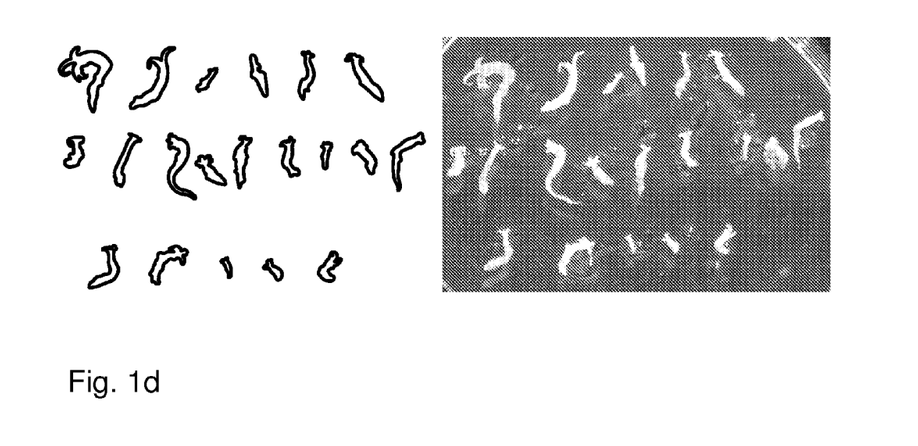

| Item | Designation of embryos before transfer to germination medium, referring to FIG. 1a and b. |
|---|---|
| (1) | width across the cotyledons |
| (2) | width one third of the way down the hypocotyl |
| (3) | width two thirds of the way down the hypocotyl |
| (4) | length of hypocotyl |
| (5) | length of root |

All references cited herein are hereby incorporated by reference in their entirety.

The expression "comprising" as used herein should be understood to include, but not be limited to, the stated items. Any intervals given should be interpreted to include the endpoint values of the give intervals.

The invention is further illustrated by the following examples, which are to be seen as non-limiting.

EXAMPLES

Example 1

The aim of the experiment was to infect somatic embryos of Norway spruce with a virus using a particle gun according to a routine method (Clapham et al. 2000: Scand. J. For. Res. 15:151-160) and derive plants containing the virus. The original standard bombardment procedure was developed for the transformation of embryogenic cultures consisting of immature embryos (i.e. proembryonic masses or PEMs). In the original protocol, from one to two hours before bombardment with gold particles coated with DNA, the cells are temporarily plasmolyzed with 0.25 M myo-inositol in proliferation medium (Table 4) to reduce damage from the penetration of the gold particles.

In the present experiment, mature embryos instead of PEMs were bombarded. The cultures of cell line 06:28:05, had been matured on standard DKM medium containing ABA for 50, days before bombardment. The embryos were exposed to medium containing 0.25, M inositol for 1-2, hours before bombardment. After bombardment the cells were unintentionally left in maturation medium containing 0.25, M inositol for 12, days, then returned to standard DKM medium containing ABA. After 8, days it was noticed that many embryos had germinated and formed healthy well developed small plantlets. About 50 plantlets with more or less well developed roots were planted out at once in pots containing mineral wool, which is not usually possible; fifteen of these survived and continued to grow. Sixty-two additional plantlets were grown aseptically on solid standard germination medium (quarter strength Schenk and Hildebrandt) to develop the root system for about 2, months; 51, of these grew well enough to plant out in pots of mineral wool. At least 48, of the plants were growing vigorously a month later. The appearance of these somatic embryo-derived plants encouraged the inventors to believe that mature embryos exposed to the relatively high concentration of inositol in the present experiment were of unusually high quality and ready for germination, without partial drying under high humidity for 2-3, weeks as in the standard procedure.

The embryos treated with inositol were strikingly more uniform and broader in relation to length, than those of the embryos from the standard protocol.

Example 2

Several experiments were performed to confirm the observations of Example 1 and to refine the novel culture method. Subsequent experiments confirm that the process of bombardment itself has no effect additional to the inclusion of 0.25, M myo-inositol in the medium. In the present experiment, embryogenic cultures of the same cell-line 06:28:05, were matured in bioreactors that enabled periodic temporary submersion in liquid DKM containing ABA. In two bioreactors, the embryos were matured for 38, days in DKM+ABA, then for 25 days in DKM+0.25, M inositol+ABA. In two control bioreactors, the cultures were maintained continuously in DKM+ABA, without the inositol treatment.

The embryos treated with inositol were strikingly more uniform, and broader in relation to length, than those of the controls. Whereas one reactor was more than sufficient to provide 130-140, high quality experimental embryos for the germination experiments, both of the control reactors were required to provide comparable numbers of good quality control embryos. Embryos from the experimental and control reactors were placed on solid germination media in petri dishes mainly to optimize germination media. Plantlet quality was assessed after 6, days' germination as 'bent' or 'not bent'. Whereas only 12, out of 134, (9%) inositol-treated embryos developed into bent plantlets, 50, out of 140, (36%) of the control embryos developed into bent plantlets. The difference was highly significant (P<0.0001) by Fisher's contingency test. The medium used for germination did not affect the results significantly.

Overall, the yield of high-quality embryos in the bioreactor experiment was therefore six to eight times greater following inositol treatment than in the untreated controls.

Example 3

Comparison of Inositol with Other Sugar Alcohols and with Sucrose

The action of 0.25, M inositol in improving somatic embryo quality is likely to be partly osmotic, partly nutritional, with cell signaling effects also involved. The inventors tested whether 0.25, M inositol could be replaced with 0.25, M of other sugar alcohols (mannitol and sorbitol) or 0.25, M extra sucrose by spreading 1.0, to 1.5, g fresh weight of embryogenic cells, cell-line 06:28:05,, on each of six plates of solid DKM+ABA maturation medium for continued growth and development over four weeks, with one subculture after 2, weeks. The cells were then subcultured onto three plates each (1.0-1.5, g cells per plate) of medium containing in addition either a) 0.25, M inositol, or b) 0.125, M mannitol and 0.125, M sorbitol, or c) 0.25, M sucrose. Control cells continued on standard medium. After three weeks, embryos of good quality were transferred to germination medium, ten embryos per petri dish, as a rough quantitative estimate of quality. The results were:

TABLE 3

| Treatment (Addition to standard medium) | Standard (no addtion) | 0.25M inositol | 0.125M mannitol plus 0.125M sorbitol | 0.25M sucrose |
|---|---|---|---|---|
| Plates with 10 high quality embryos | 2 | 6 | 3 | 0 |

The standard treatment gave a low yield of quality embryos because of poor synchrony of development. The sugar alcohols all worked well, but inositol gave about twice as many embryos of good quality as mannitol plus sorbitol. 0.25, M sucrose had a clearly detrimental effect on embryo quality; the embryos were less developed, less elongated, often reddish, indicating stress. Embryo quality was too poor to merit subculture and further studies.

Example 4

To investigate how various inositol concentrations synchronize embryo development and affect the quality of the developing embryos, three cell-lines of embryogenic callus of Norway spruce, cell-lines 61:21, 19:01, and 28:05, were exposed to 1, week on prematuration medium, and matured for 40, days, 36, days or 33, days, respectively on maturation medium with subculturing every two weeks. Small clumps about 1, cm diameter of maturing embryos were then subcultured on maturation medium containing 0.0005, M (here denoted 0, M), 0.06, M, 0.1, M, 0.2, M, 0.25, M or 3, M inositol.

Twenty individual mature embryos or small plantlets were picked randomly from the plates and the following measurements were taken, for quality measurement, see FIG. 1: width of hypocotyls (1), width across the cotyledons one third of the way down of the hypocotyls (2), width across the cotyledons two third of the way down of the hypocotyls (3) and length of the hypocotyls (4), length of root (5).

Figure 2A:
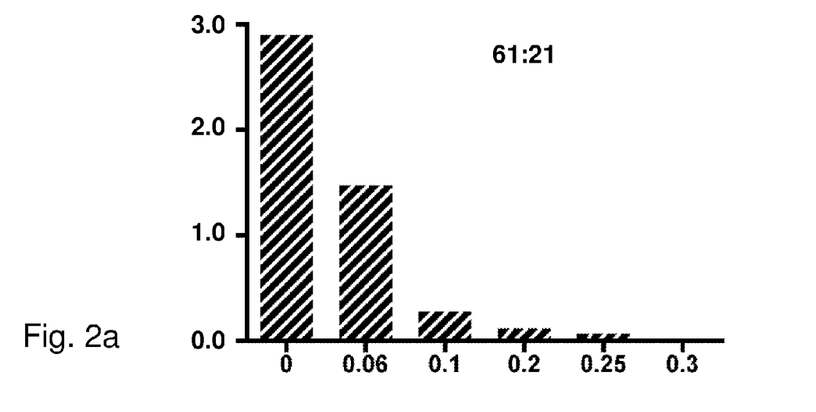
FIGS. 2a-c, depicts graphs representing the root length in relation to sugar alcohol concentration in three different embryogenic cell lines from Norway spruce. Y-axis represents root length (5) in millimetres [mm].

Good and high quality somatic embryos should not have developed a root (5), see FIG. 1b, and FIG. 2a, to c.

Figure 2B:
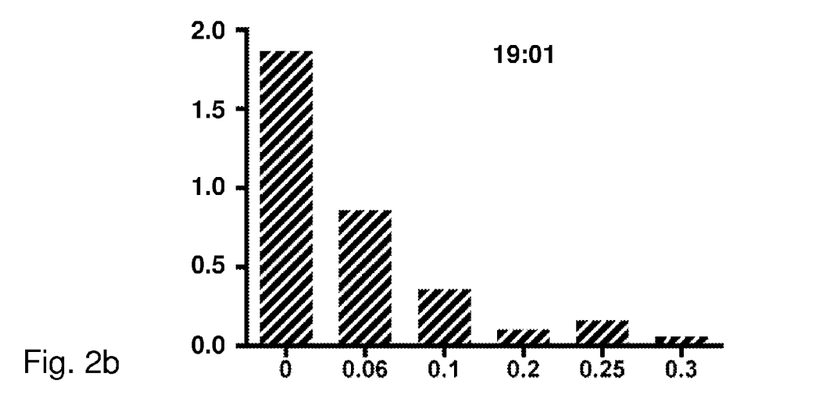
Figure 2C:
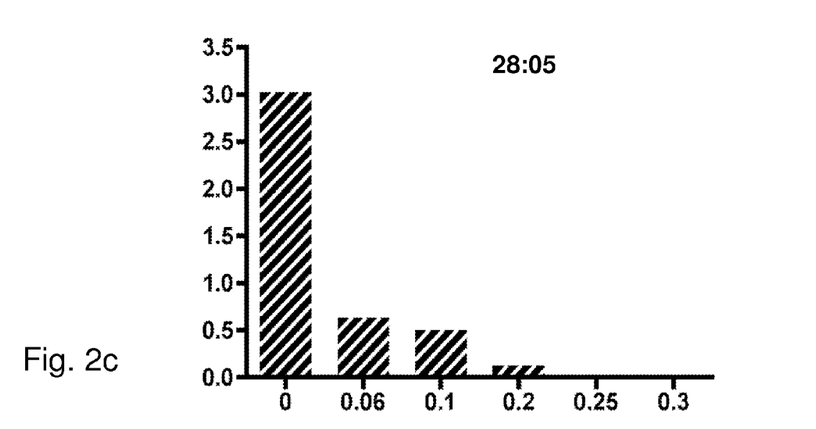

Root development, indicating premature germination, is present at low concentrations of inositol but is inhibited almost completely at concentrations in the range 0.2-0.3, M, FIG. 2a-c. This is an attractive situation since root development at this premature stage results in delicate, poorly developed plantlets.

Furthermore, good and high quality somatic embryos have low variation in length of hypocotyls (1). This can be seen in FIG. 3a, to c.

Figure 3A:
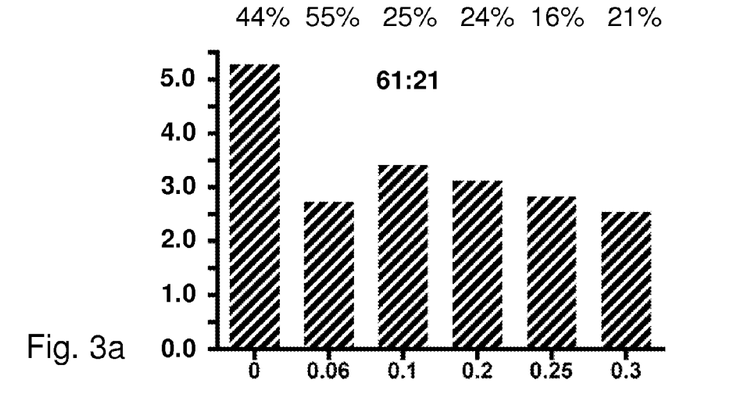
FIGS. 3a-3c, depicts graphs representing the hypocotyl length and the coefficient of variation of hypocotyls length in relation to sugar alcohol concentration in three different cell lines from Norway spruce. Y-axis represents hypocotyl length (4) in millimetres [mm].
Figure 3B:
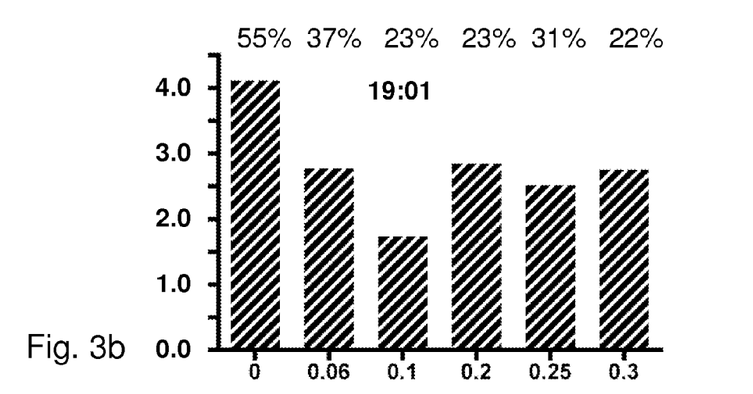
Figure 3C:
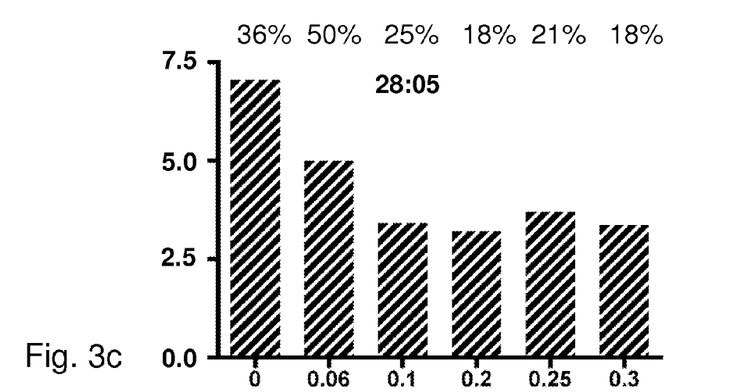

A measurement of the synchrony of development is the coefficient of variation of the hypocotyl length FIG. 3a-c. For cell-line 61:21,, the coefficient of variation of hypocotyl length is at a minimum at 0.25, M inositol concentration, indicating that synchrony of development is maximal at 0.25, M inositol. Similarly for the other two cell-lines, the variation in hypocotyl length was reduced markedly at the higher concentrations of inositol.

Figure 4:
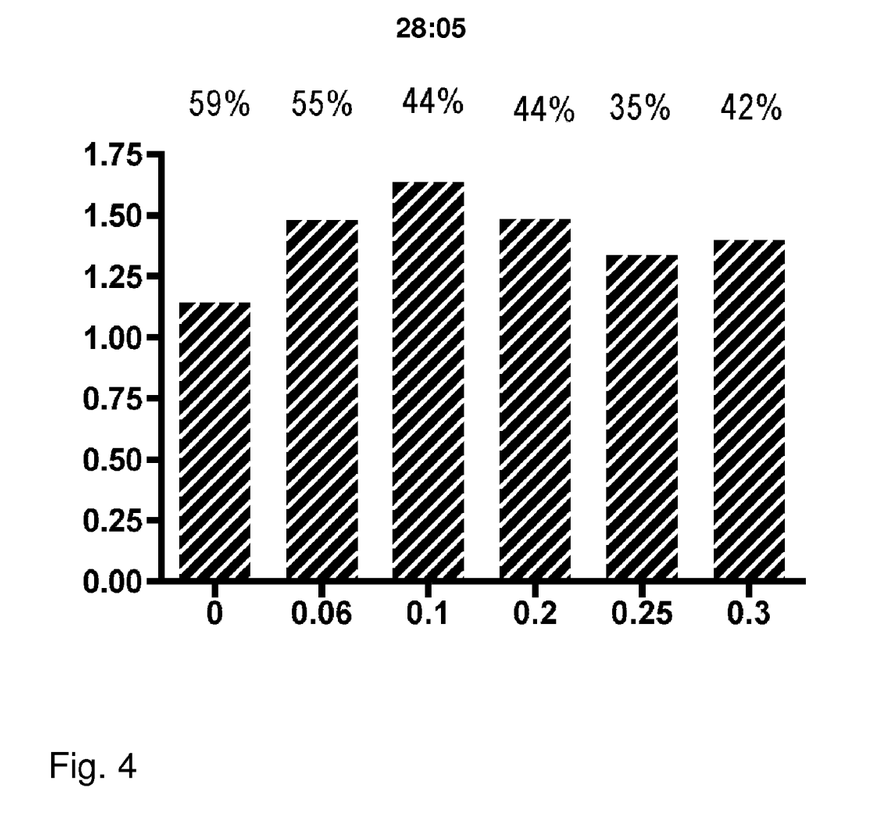
FIG. 4 depicts a graph representing width across cotyledon in relation to sugar alcohol concentration and coefficient of variation thereof. Y-axis represents the width across cotyledons (1) in millimetres [mm].

A further measure of the synchrony of development is the width across the cotyledons (1). For cell-line 28:05, the coefficient of variation is at a minimum, 35%, after 0.25, M inositol, FIG. 4. The figure also confirms that the higher inositol concentrations allow development of the embryos, as measured by distance across the cotyledons, while inhibiting germination.

Figure 5A:
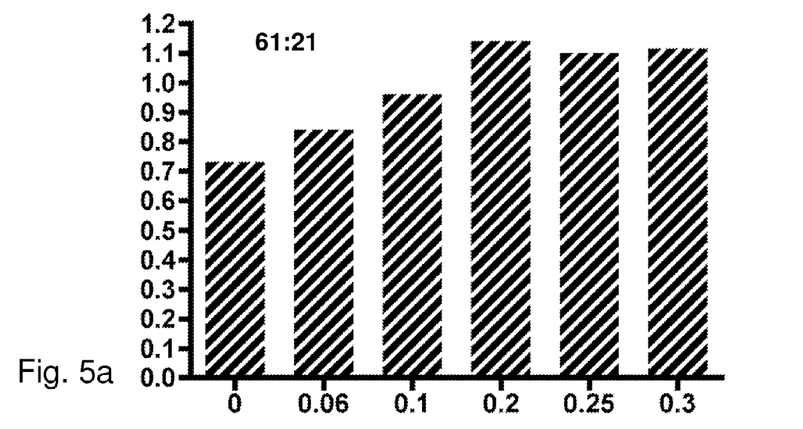
FIGS. 5a-5c, depicts graphs representing width ratios in relation to sugar alcohol concentration in three different embryogenic cell lines from Norway spruce. Y-axis represents the width ratio.
Figure 5B:
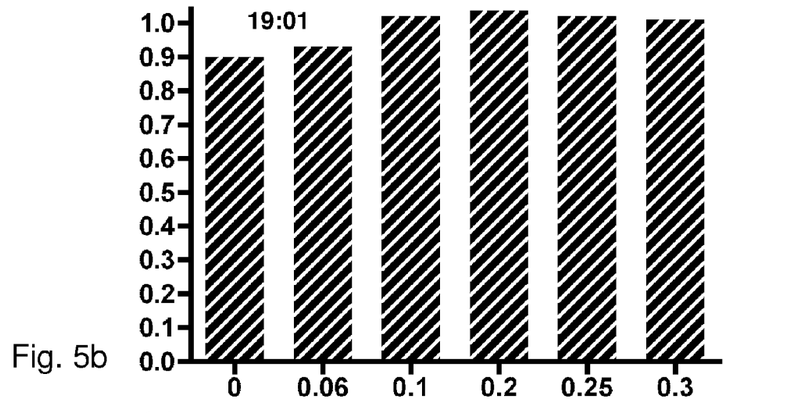
Figure 5C:
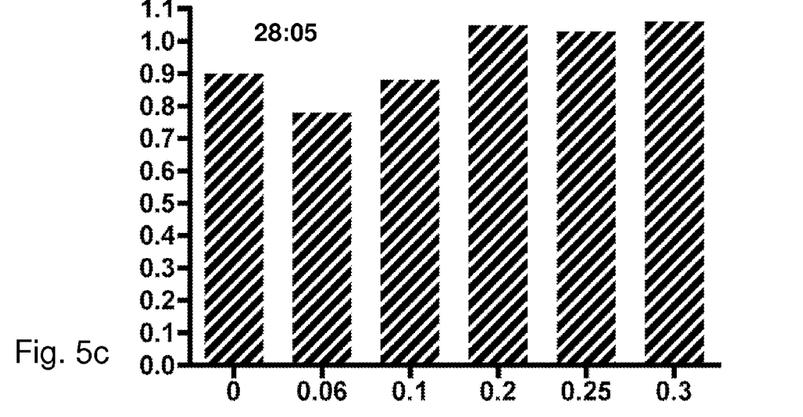

A further estimate of the quality of the synchronized embryos is the ratio of the width one third up down the hypocotyl (2) to the width two thirds down the hypocotyl (3). In poorly developed embryos, there is a tendency to constriction in the hypocotyl near the cotyledons and/or a swelling at the base of the hypocotyl, so that the ratio of widths is below about unity. In well developed embryos the ratio is just above unity. This favorable ratio is achieved at concentrations in the range 0.2-0.3, M inositol FIG. 5a-c.

In summary, concentrations of inositol in the range 0.2-0.3, M synchronized development of the embryos by inhibiting germination but not embryo development, so that mature, high quality embryos are accumulated.

Furthermore the experiments showed that the effect is not restricted to one particular cell line.

Example 5

Figure 6A:
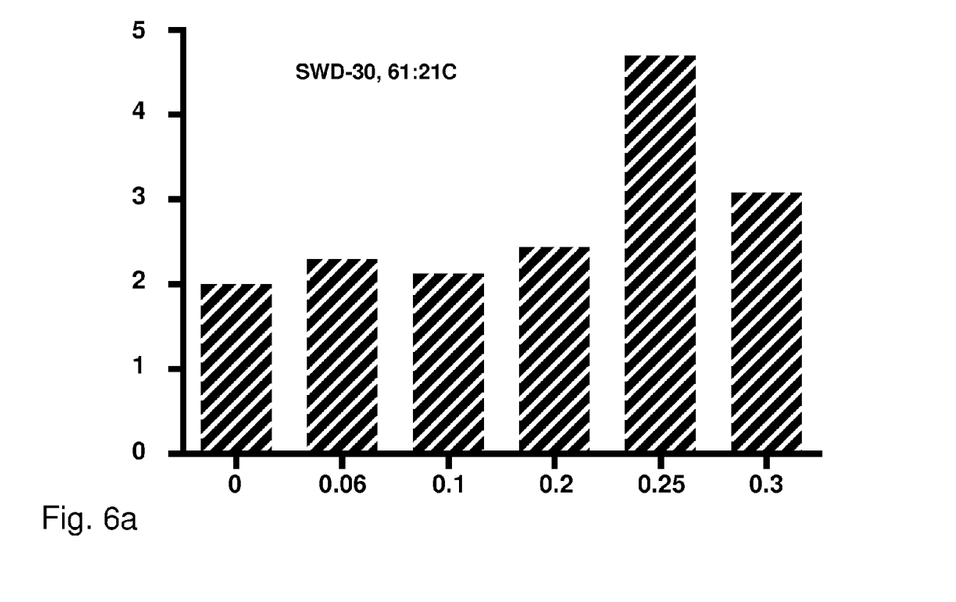
FIGS. 6a-6d, depicts graphs representing root length after 11, days on germination medium in relation to sugar alcohol concentration in four different cell lines from Norway spruce. Y-axis represents root length (5) in millimetres [mm].
Figure 6B:
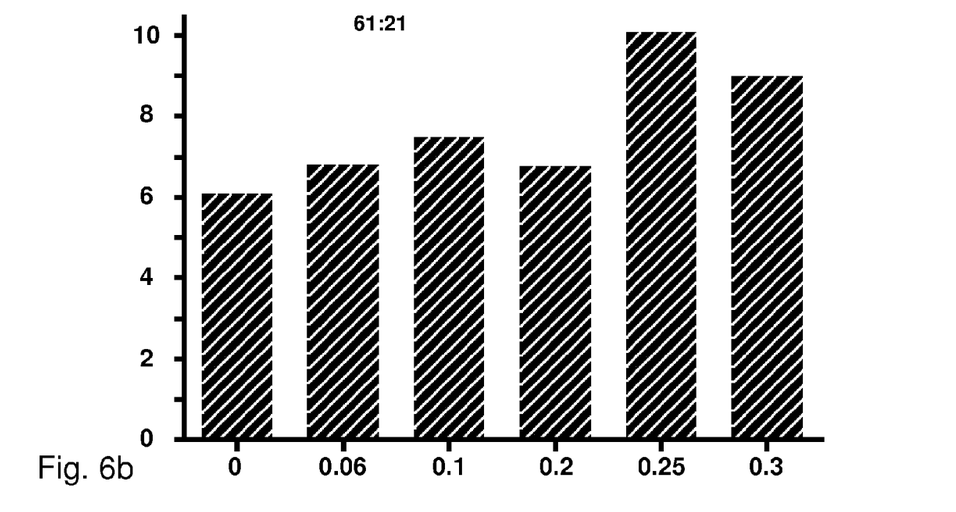

To further confirm the quality of embryos treated with 0.25, M inositol, and to show that after inositol treatment, the standard procedure of drying the embryos at high humidity before germination is unnecessary, material of cell-line 95:61:21, was cultured as above except that the treatment with inositol at various concentrations was for 17, days. Then 15, embryos from each concentration of inositol were transferred to germination medium (same as the prematuration medium). The progress of germination was measured by root length after 11, days on germination medium. Germination was fastest for the embryos that had been treated with 0.25, M inositol FIG. 6a. The difference between the root lengths after treatment at the three highest concentrations compared with those at the three lowest concentrations was highly significant by t-test (P<0.001). The experiment was repeated with another replicate of cell-line 61:21. This time, the inositol treatment was for 25, days, the small clumps of embryos were transferred to prematuration medium for 9, days, then 10, embryos were individually planted on prematuration medium and root length was measured 29, days later. The relative results were as before, with embryos treated with 0.25, M rooting fastest FIG. 6b;, the precise length of time of exposure to high concentrations of inositol over the range 15-40, days is not critical, which is of practical advantage.

Figure 6C:
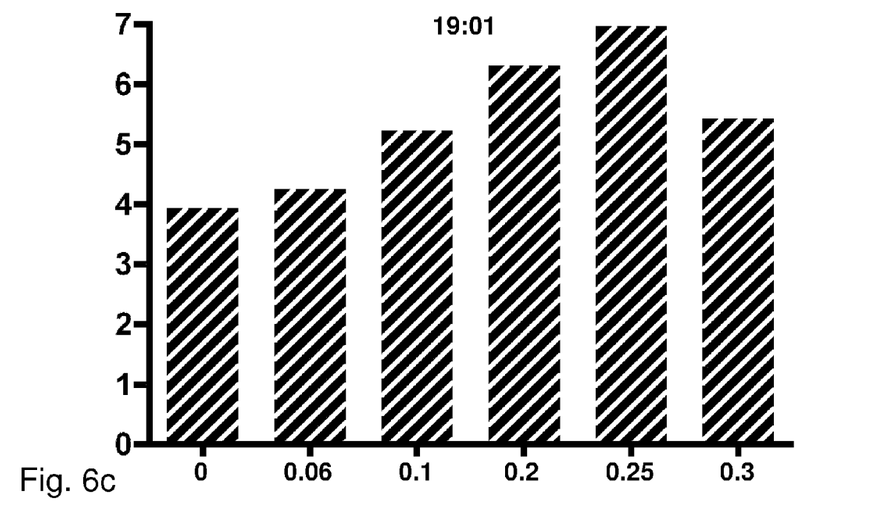
Figure 6D:
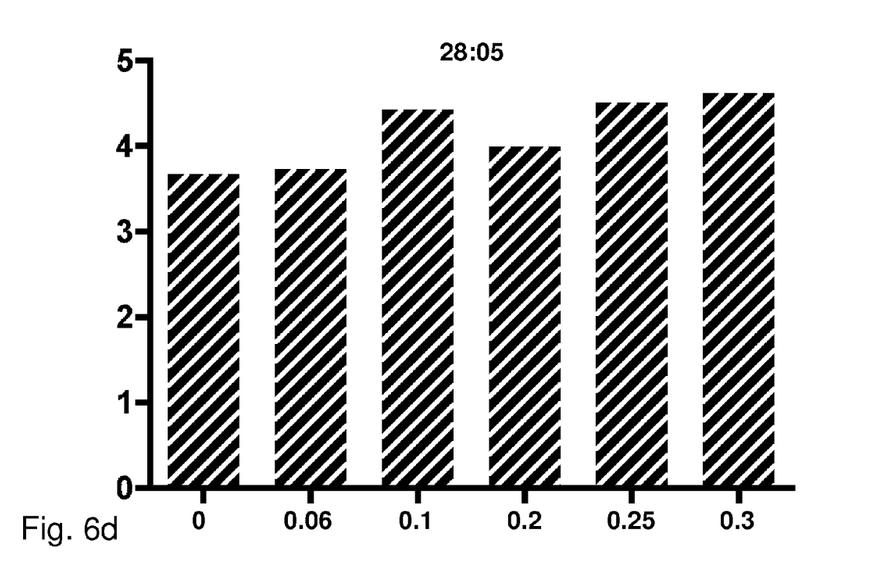
Figure 7:
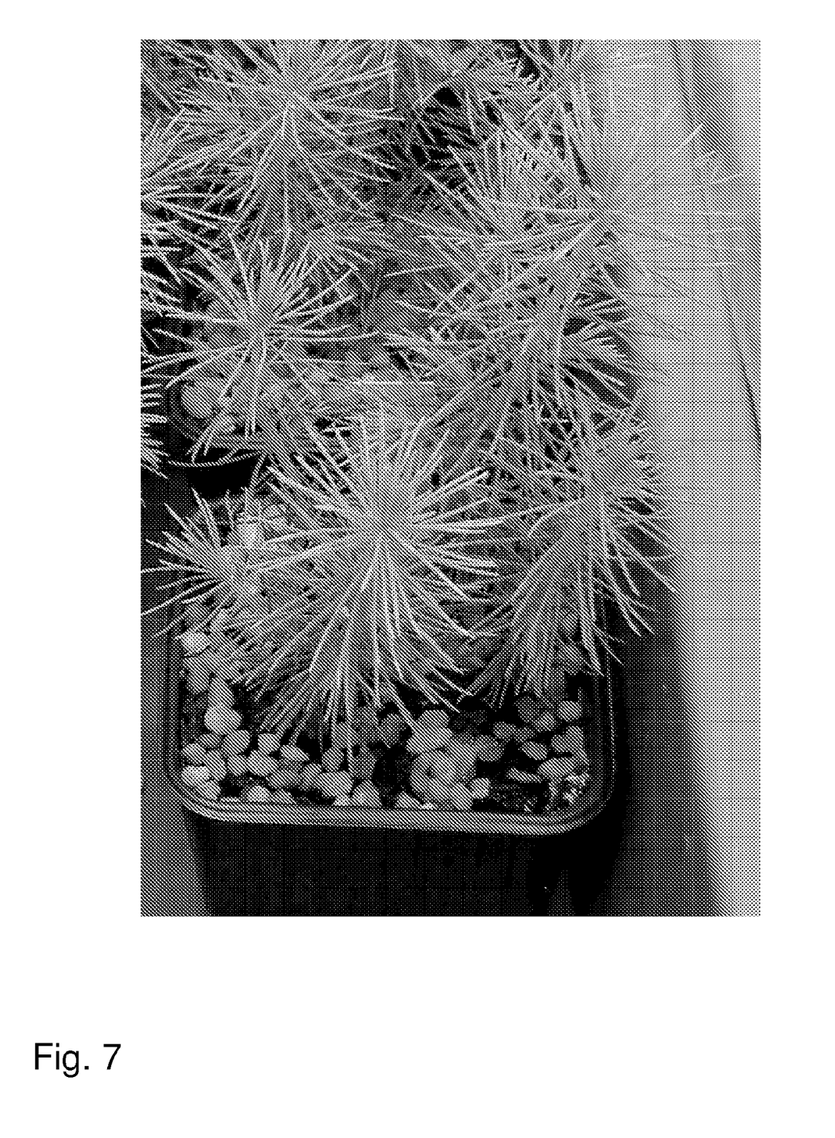
FIG. 7 shows healthy plants derived from embryogenic mass with a method of the invention.

Two additional cell-lines, 19:01, and 28:05,, were studied, confirming the advantages of treatment with high concentrations of inositol for subsequent root growth on germination medium FIGS. 6c, and 6d. The length of inositol treatment was 16, days for both lines. Root length was measured 12, or 14, days according to cell-line after transfer of 20, embryos for each concentration of inositol to prematuration medium for germination.

For all four experiments of Example 5,, root length after treatments of 0.2, to 0.3 M inositol was compared to root length after treatments with 0, to 0.1, M inositol in a paired t-test. Root length was significantly greater after treatment at the three highest inositol concentrations, P<0.03.

The inventors have compared on a small scale the germination of inositol-treated embryos with partially dried embryos that have been matured by standard procedures. Roots develop a few days earlier after drying, but shoots grow faster and more vigorously from inositol-treated embryos.

Embryos of cell-line 28:05, treated with 0.25, M inositol and germinated in vitro as described above were grown on in stonewool in plastic pots 8×8×10, cm with standard commercial mineral nutrition in a growth chamber in continuous light at 20° C. for three months. The plants were vigorous and healthy. The treatment with high concentrations of inositol has no unexpected longer term effects on subsequent growth.

Example 6

In order to verify the broad use of the newly invented method, additional conifers have been tested by adapting the methods of Examples 4, and 5. Embryogenic callus of Scots pine, *Pinus sylvestris*,, cell-line 42:6:3,, was proliferated on DCR medium (Burg et al. 2007:, J. Exp. Bot. 58: 687-698) containing 2,4-D and BA at the same concentrations as described for spruce. The cells were taken through the early maturation step on DCR medium containing 7.5% polyethylene glycol 400, 3% maltose (replacing sucrose) and 16, mg per liter abscisic acid (Burg et al. 2007:, J. Exp. Bot. 58: 687-698). Samples of cells were then exposed to the same medium containing inositol at concentrations of 0.0005, M 0.1, M, 0.2, M, 0.25, M, 0.3, M or 0.5 M for four weeks. As with spruce, embryos continued to mature on concentrations of inositol in the range 0.2-0.3, M while precocious germination was inhibited, so that synchronization was enhanced. On the media containing 0.0005, M inositol, and 0.1 M inositol, some of the embryos showed characteristic signs of premature germination such as hypocotyl extension and greening of the cotyledons.

Somatic embryogenesis is more problematic in pine than in spruce, so that experiments with mature embryos were on a small scale. Nevertheless, by germinating groups of ten embryos on DKM medium, we could establish that the embryos exposed to 0.25, M inositol were in better condition than those exposed to 0.0005, M inositol. Whereas the embryos that had grown on 0.0005, M inositol all developed a red colour under the cotyledons within two days of germination on DKM, indicating stress, the embryos exposed to 0.25, M inositol showed no such signs of stress. Furthermore, a higher proportion of the embryos that had been exposed to 0.25, M inositol developed healthy roots on the germination medium. Exposure to 0.5 M inositol inhibited further maturation of the embryos.

Corresponding experiments with Mexican Yellow Pine, *Pinus oocarpa*, line 2, showed the same tendencies. Experiments with Loblolly pine, *P. taeda*,, are in progress.

Materials

Table 4. Composition of media. LP×½ was used for proliferation of embryogenic cultures. DKM medium was used (a) for prematuration, (b) for initial maturation in medium supplemented with ABA (8 mg L-1) and (c) for final maturation in medium supplemented with enhanced concentrations of sugar alcohols or sucrose. The cells were cultured either in the air with temporary immersion in the liquid medium, or on solid medium containing gelrite (3.5 g L-1)

| Medium Compound | LP × ½ Weight/L | Conc | DKM Weight/L | Conc |
|---|---|---|---|---|
| $KNO_3$ | 0.95 g | 9.40 mM | 2.34 g | 23.14 mM |
| $NH_4NO_3$ | 0.16 g | 2.00 mM | 0.276 g | 3.45 mM |
| $MgSO_4 \cdot 7H_2O$ | 0.185 g | 0.75 mM | 0.38 g | 1.54 mM |
| $KH_2PO_4$ | 0.17 g | 1.25 mM | 0.085 g | 0.62 mM |
| $CaCl_2 \cdot 2H_2O$ | 0.22 g | 1.50 mM | 0.22 g | 1.50 mM |
| Na•Fe-EDTA | 0.0092 g | 0.03 mM | 0.092 g | 0.13 mM |
| Na•Zn-EDTA | 2.358 mg | 0.01 mM | — | — |
| $ZnSO_4 \cdot 7H_2O$ | — | — | 8.6 mg | 0.03 mM |
| $MnSO_4 \cdot 7H_2O$ | 8.45 mg | 0.03 mM | 30 mg | 0.11 mM |
| $H_3BO_3$ | 0.315 mg | 0.01 mM | 6.2 mg | 0.10 mM |
| $NaMoO_4 \cdot 2H_2O$ | 0.0125 mg | 0.057 µM | 0.25 mg | 1.14 µM |
| $CuSO_4 \cdot 5H_2O$ | 0.00125 mg | 0.005 µM | 0.025 mg | 0.10 µM |
| $CoCl_2 \cdot 6H_2O$ | 0.00125 mg | 0.006 µM | 0.025 mg | 0.12 µM |
| KI | 0.375 mg | 2.26 µM | 0.83 mg | 5.00 µM |
| Pyridoxine | 0.5 mg | 2.43 µM | 0.5 mg | 2.43 µM |
| Nicotinic acid | 0.5 mg | 4.06 µM | 0.5 mg | 4.06 µM |
| Thiamine•HCl | 2.5 mg | 0.01 mM | 1 mg | 3.0 µM |
| Myo-inositol | 50 mg | 0.28 mM | 100 mg | 0.56 mM |
| Casein hydrolysate | — | — | 0.5 g | |
| Sucrose | 10 g | 29.21 mM | 30 g | 87.6 mM |
| ABA (2,4-dichlorphenoxy acetic acid) | 2.21 mg | 10.00 µM | — | — |
| BA (benzyladenine) | 1 mg | 4.44 µM | — | — |
| Invented medium additional components | | | | |
| Alt. 1: Myo-inositol | | | 45 g | 0.25M |
| Alt 2: Mannitol | | | 45.6 g | 0.25M |
| Alt 3: Sorbitol | | | 45.6 g | 0.25M |
| Alt 4: Mannitol + Sorbitol | | | 22.8 g/22.8 g | 0.125M/0.125M |

The invention claimed is:

1. A method for maturing prematurated somatic plant embryos of a conifer species in culture comprising the step of:
   (a) contacting said prematurated somatic plant embryos with a culture medium comprising 0.2-0.3 M of inositol; and
   (b) culturing said prematurated somatic plant embryos in said culture medium for a time period such that the desired level of maturation is achieved.

2. The method according to claim 1, wherein the inositol is a steroisomer myo-inositol.

3. The method according to claim 1, wherein the prematurated somatic plant embryos at the time of contacting with the culture medium are prematurated somatic plant embryos having undergone a prematuration stage.

4. The method according to claim 1, wherein the prematurated somatic plant embryos lack root meristems at the time of contacting with the culture medium.

5. The method according to claim 1, wherein the prematurated somatic plant embryos at the time of contacting with the culture medium are prematurated somatic embryos not yet having fully undergone a germination stage.

6. The method according to claim 1, wherein the prematured somatic plant embryos lack roots at the time of contacting with the culture medium.

7. The method according to claim 1, wherein the prematurated somatic plant embryos are of a conifer species selected from the group consisting of Norway spruce, Norway pine, and loblolly pine.

8. The method according to claim 1, wherein premature germination of the prematurated somatic plant embryos is inhibited.

9. The method according to claim 1, wherein the maturation of the individual prematurated somatic plant embryos is synchronized.

10. The method according to claim 1, wherein uniform quality of the prematurated somatic plant embryos is achieved.

11. The method according to claim 1, wherein uniform quality and synchronized development of prematurated somatic plant embryos-derived plantlets is achieved.

12. The method according to claim 11, wherein the plantlets are plantlets planted in a substrate.

13. A method for producing plantlets from plant embryogenic mass of a conifer species, comprising the steps of:
   (a) producing prematurated somatic embryos from the plant embryogenic mass;
   (b) maturating the prematurated somatic plant embryos using a method comprising:
      (1) contacting said prematurated somatic plant embryos with a culture medium comprising 0.2-0.3 M of inositol; and
      (2) culturing said prematurated somatic plant embryos in said medium for a time period such that the desired level of maturation is achieved; and
   (c) germinating the maturated somatic plant embryos and converting the germinated somatic plant embryos to platelets, wherein no partial drying of the maturated somatic plant embryos takes place between the maturation and germination.

* * * * *